(12) United States Patent
Kanada (10) Patent No.: US 9,898,843 B2
(45) Date of Patent: Feb. 20, 2018

(54) GRAPH DISPLAY APPARATUS, ITS OPERATION METHOD AND NON-TRANSITORY COMPUTER-READABLE RECORDING MEDIUM HAVING STORED THEREIN GRAPH DISPLAY PROGRAM

(71) Applicant: FUJIFILM Corporation, Tokyo (JP)

(72) Inventor: Shoji Kanada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 242 days.

(21) Appl. No.: 14/863,462

(22) Filed: Sep. 24, 2015

(65) Prior Publication Data

US 2016/0012620 A1    Jan. 14, 2016

Related U.S. Application Data

(63) Continuation of application No. PCT/JP2014/000360, filed on Jan. 24, 2014.

(30) Foreign Application Priority Data

Mar. 28, 2013    (JP) .................................. 2013-068218

(51) Int. Cl.
*G06T 11/20* (2006.01)
*G06K 9/52* (2006.01)
(Continued)

(52) U.S. Cl.
CPC .............. *G06T 11/206* (2013.01); *G06K 9/52* (2013.01); *G06Q 50/24* (2013.01); *G06T 7/0012* (2013.01); *G06T 7/60* (2013.01)

(58) Field of Classification Search
CPC .................................................... G06T 11/206
See application file for complete search history.

(56) References Cited

U.S. PATENT DOCUMENTS

2007/0161600 A1* 7/2007 Helenek ............... A61K 31/715
514/54
2007/0213109 A1* 9/2007 Sato ........................ A63F 13/10
463/3

(Continued)

FOREIGN PATENT DOCUMENTS

| JP | H6-083880 | 3/1994 |
| JP | 2011-238029 | 11/2011 |
| JP | 2012-127762 | 7/2012 |

OTHER PUBLICATIONS http://gnuplot-surprising.blogspot.com/2011/10/broken-axes-graph-in-gnuplot-3.html.*

(Continued)

*Primary Examiner* — Kee M Tung
*Assistant Examiner* — Grace Q Li
(74) *Attorney, Agent, or Firm* — JCIPRNET (57) ABSTRACT

When line graphs are displayed on coordinates having a horizontal axis as a time axis and a vertical axis as an axis representing examination values, a line graph is generated in such a manner that data points representing examination data are connected to each other by a line in a case where a time interval between examinations temporally next to each other is less than a maximum line-connection interval for an examination item, and in such a manner that data points representing examination data are not connected to each other in a case where the time interval between examinations temporally next to each other exceeds the maximum line-connection interval for the examination item. Plural line graphs overlapping with each other are displayed on the coordinates.

8 Claims, 6 Drawing Sheets

(51) Int. Cl.
*G06T 7/00* (2017.01)
*G06T 7/60* (2017.01)
*G06Q 50/24* (2012.01)

(56) References Cited

U.S. PATENT DOCUMENTS

2008/0161658 A1* 7/2008 Tashiro .............. G06F 19/3418
 600/301
2011/0282662 A1 11/2011 Aonuma et al.
2013/0110856 A1* 5/2013 Ota ................... G06F 17/30973
 707/758

OTHER PUBLICATIONS

Takahiro Fujii et al., "Feature: Efficient Large Intestine Cancer Examination Interval", Digestive Organ Endoscope, Kabushiki Kaisha Tokyo Igakusha, vol. 14, No. 4, pp. 439-445, Apr. 2002. An English abstract is located at the end of the article.
"Written Opinion of the International Searching Authority (PCT/ISA/237) of PCT/JP2014/000360", dated Apr. 22, 2014, pp. 1-4, with a partial English translation thereof.
"Office Action of Japan Counterpart Application" with machine English translation, dated May 10, 2016, p. 1-p. 5.

* cited by examiner

FIG.7

GRAPH DISPLAY APPARATUS, ITS OPERATION METHOD AND NON-TRANSITORY COMPUTER-READABLE RECORDING MEDIUM HAVING STORED THEREIN GRAPH DISPLAY PROGRAM

CROSS-REFERENCE TO RELATED APPLICATIONS

This application is a Continuation of PCT International Application No. PCT/JP2014/000360 filed on Jan. 24, 2014, which claims priority under 35 U.S.C. § 119(a) to Japanese Patent Application No. 2013-068218 filed on Mar. 28, 2013. Each of the above applications is hereby expressly incorporated by reference, in its entirety, into the present application.

BACKGROUND

The present disclosure relates to a graph display apparatus for displaying examination results of plural examinations performed on a patient by line graphs, an operation method of the graph display apparatus, and a non-transitory recording medium having stored therein a graph display program.

In medical fields of recent years, when diagnosis is performed on a patient, plural results of examinations performed on the patient are displayed and used as reference information for diagnosing a disease name, deciding a treatment policy or the like.

There are many kinds of examination performed on patients. In actual clinical scenes, when a patient is suspected of a specific disease, a doctor performs diagnosis or treatment by referring to each examination result of plural examinations that are considered to be important to diagnose the specific disease. However, it is difficult to display all the results of examinations performed on the patient because the size of a display is limited. Further, if too much information is displayed on a display screen, that will become even a negative factor as observation becomes rather difficult.

In conventional systems, an operator selected important results or results in which he/she had interest from results obtained by examinations, and the results were displayed by graphs. Further, items to be displayed together with the graphs were selected by the operator from many items of treatment performed on the patient (medication and injection). Therefore, some methods were proposed to reduce the work of operators. In the methods, conditions for displaying the content of treatment and a change in examination results were determined by managing items to be displayed by graphs, display modes and the like for each disease (for example, Japanese Unexamined Patent Publication No. 6(1994)-083880 (Patent Document 1)).

SUMMARY

Each disease has necessary examination items. However, even if a patient has the same disease, vital examinations must be performed many times every day while the patient is hospitalized, and a short-term course of the condition of the patient must be recognized. Meanwhile, some other examinations are performed every few days or every few months. Therefore, an interval of examination is different, depending on the examination. When changes in such examinations performed at different examination intervals are checked, it is necessary to check a tendency in a display period appropriate for checking the result of each examination by switching display periods of graphs. Especially, in circulatory diseases and diseases of kidneys, many examination results must be checked to make judgments, and too many graphs are displayed. When a long-term course of the condition of a patient is observed in such a state, if graphs of vital data including many pieces of examination data are present, there is a problem that it becomes difficult to find a change for observing the long-term course because of the presence of vital data.

In the method of Patent Document 1, conditions for displaying the content of treatment and a change in examination data were determined by managing items to be displayed by graphs, display modes and the like for each disease. However, when both of a graph of vital data including many pieces of examination data and a graph of examination data for observing a long-term course were present, it was impossible to prevent observation of the graphs from becoming difficult.

In view of the foregoing circumstances, the present disclosure provides a graph display apparatus that generates graphs representing changes of examination data in plural examinations in such a manner that the changes of examination data in the plural examinations are recognizable, an operation method of the graph display apparatus, and a non-transitory recording medium having stored therein a graph display program.

A graph display apparatus of the present disclosure displays, on coordinates having a horizontal axis and a vertical axis, one of which is a time axis and the other one is an axis of examination values, line graphs connecting data points representing examination data about a patient by lines in order of time of examination for plural examination items. The apparatus includes a maximum line-connection interval determination means that determines, for each of the plural examination items, a maximum line-connection interval that is a longest time interval between examinations temporally next to each other to connect data points representing examination data for the each of the plural examination items to each other, a line graph generation means that generates a line graph for each of the plural examination items in such a manner that data points representing examination data are connected to each other in a case where a time interval between examinations temporally next to each other is less than or equal to the maximum line-connection interval for the each of the plural examination items, and in such a manner that data points representing examination data are not connected to each other in a case where the time interval between examinations temporally next to each other exceeds the maximum line-connection interval for the each of the plural examination items, and a graph display means that displays the line graphs on the coordinates.

An operation method of a graph display apparatus of the present disclosure is an operation method of a graph display apparatus that displays, on coordinates having a horizontal axis and a vertical axis, one of which is a time axis and the other one is an axis of examination values, line graphs connecting data points representing examination data about a patient by lines in order of time of examination for plural examination items. The operation method includes a maximum line-connection interval determination step in which a maximum line-connection interval determination means determines, for each of the plural examination items, a maximum line-connection interval that is a longest time interval between examinations temporally next to each other to connect data points representing examination data for the each of the plural examination items to each other, a line graph generation step in which a line graph generation means generates a line graph for each of the plural examination items in such a manner that data points representing examination data are connected to each other in a case where a time interval between examinations temporally next to each other is less than or equal to the maximum line-connection interval for the each of the plural examination items, and in such a manner that data points representing examination data are not connected to each other in a case where the time interval between examinations temporally next to each other exceeds the maximum line-connection interval for the each of the plural examination items, and a graph display step in which a graph display means displays the line graphs on the coordinates.

A non-transitory recording medium of the present disclosure is a non-transitory recording medium having stored therein a graph display program that causes a computer of a graph display apparatus that displays, on coordinates having a horizontal axis and a vertical axis, one of which is a time axis and the other one is an axis of examination values, line graphs connecting data points representing examination data about a patient by lines in order of time of examination for plural examination items to function as a maximum line-connection interval determination means that determines, for each of the plural examination items, a maximum line-connection interval that is a longest time interval between examinations temporally next to each other to connect data points representing examination data for the each of the plural examination items to each other, a line graph generation means that generates a line graph for each of the plural examination items in such a manner that data points representing examination data are connected to each other in a case where a time interval between examinations temporally next to each other is less than or equal to the maximum line-connection interval for the each of the plural examination items, and in such a manner that data points representing examination data are not connected to each other in a case where the time interval between examinations temporally next to each other exceeds the maximum line-connection interval for the each of the plural examination items, and a graph display means that displays the line graphs on the coordinates.

Further, the maximum line-connection interval determination means may obtain, for each of the plural examination items, examination intervals between examinations performed on plural patients, and set, for each of the plural examination items, examination intervals within a predetermined range from an average or a median of the obtained examination intervals, as standard examination intervals, and determine a time interval within a predetermined range from a maximum value of the standard examination intervals, as the maximum line-connection interval.

Further, it is desirable that the graph display means displays an area in a time period without any connection line in all the line graphs for the plural examination items in such a manner that a length on a time axis for a unit time is reduced, or in such a manner that the area in the direction of the time axis is shortened by cutting.

Further, the maximum line-connection interval may be determined according to a disease.

According to the present disclosure, when line graphs connecting data points representing examination data about a patient in order of time of examination are generated for plural examination items, a maximum line-connection interval that is a longest time interval to connect data points representing examination data to each other is determined in advance, and a line graph is generated in such a manner that data points representing examination data are connected to each other in a case where a time interval between examinations temporally next to each other is less than or equal to the maximum line-connection interval, and in such a manner that data points representing examination data are not connected to each other in a case where the time interval between examinations temporally next to each other exceeds the maximum line-connection interval. Therefore, data points are not connected to each other by a line in a part in which examinations for observing a short-term change, such as vital data, are not performed for a long period of time. Hence, it is possible to observe a change in examination data for observing a long-term course without interference of graphs having short-term changes. Consequently, it is possible to greatly reduce a drop in visual recognizability.

Further, statistics on time intervals at which each examination was performed on plural patients may be collected, and a maximum line-connection interval may be determined based on the longest examination interval among standard examination intervals at which examination was performed. Then, it is possible to connect data points to each other in conformity with the actual examination interval at which each examination is performed.

Further, a time period without any connection line in graphs is a time period without any meaningful data. Therefore, in the present disclosure, the graphs may be displayed in such a manner that such a time period is reduced, or in such a manner that such a time period is shortened by cutting. Then, it is possible to display a change in data for a longer period of time on a display screen, and to easily check a clinical history in the past.

Further, the maximum line-connection interval may be determined for each examination item according to a disease, instead of being determined for each examination item. Then, most appropriate display in which a difference in characteristics of each disease is taken into consideration is possible.

DESCRIPTION OF THE PREFERRED EMBODIMENTS

Figure 1:
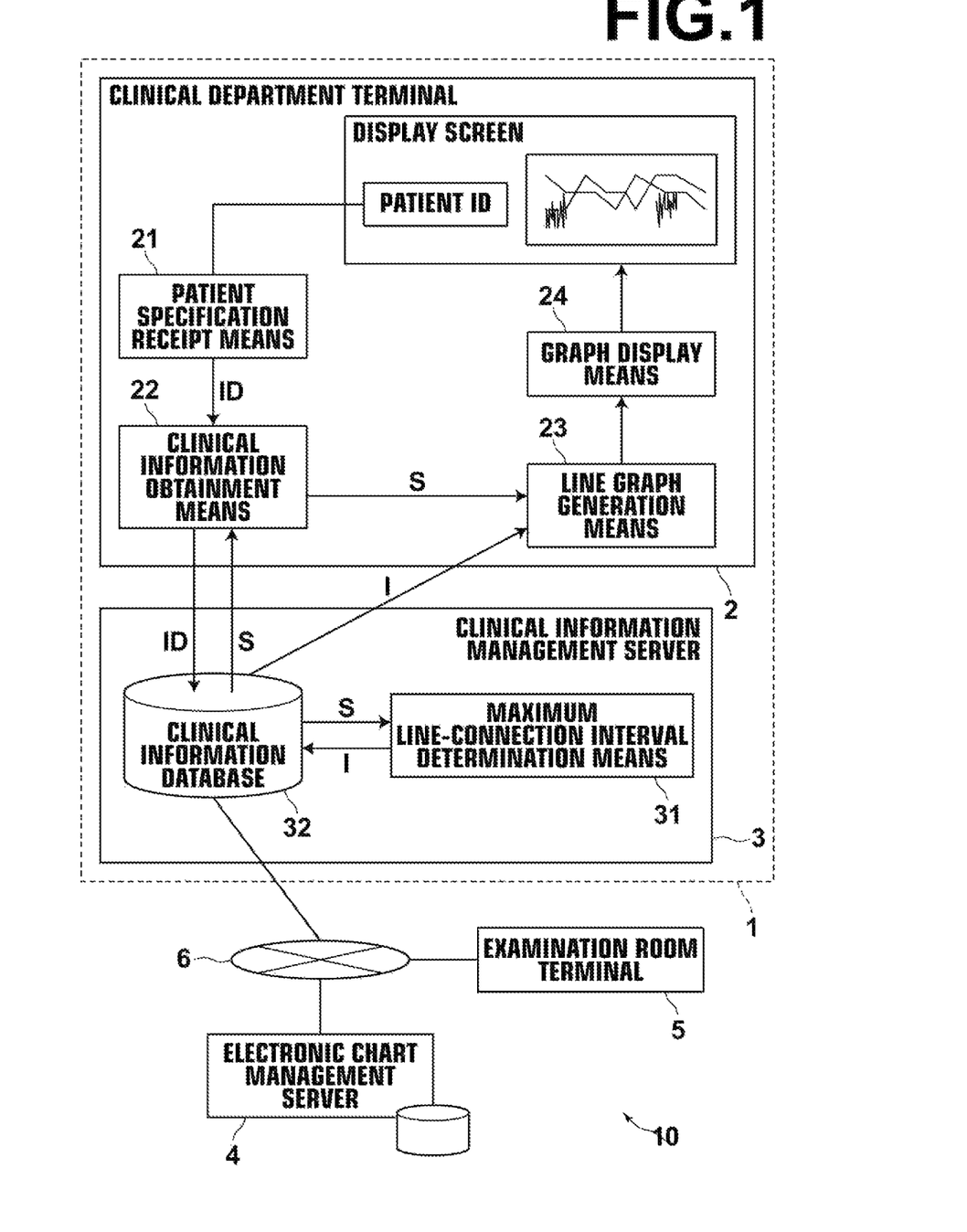
FIG. 1 is a schematic diagram illustrating the configuration of a clinical information system to which a graph display apparatus according to an embodiment of the present disclosure has been applied.

Hereinafter, embodiments of a graph display apparatus of the present disclosure will be described with reference to FIG. 1. FIG. 1 is a schematic diagram illustrating the configuration of a clinical information system to which a graph display apparatus according to an embodiment of the present disclosure has been applied.

As illustrated in FIG. 1, a clinical information system 10 includes a clinical department terminal 2, a clinical information management server 3, an electronic chart management server 4 and an examination room terminal 5, which are connected to each other through a network 6 in such a manner that they can communicate with each other.

The electronic chart management server 4 is a computer including an electronic chart database in which electronic charts are stored. An operating system and software for managing the database have been installed in the electronic chart management server 4. Further, software for retrieving, based on a request by the clinical department terminal 2 or the like, clinical information S, such as examination data, related to each electronic chart, and sending and receiving a retrieval result has been installed in the electronic chart management server 4. The electronic chart management server 4 is connected to the clinical information management server 3, the clinical department terminal 2, the examination room terminal 5 and the like through the network 6 in such a manner that each clinical information S recorded in an electronic chart is obtainable.

The examination room terminal 5 is a computer installed in an examination room that is separate from each clinical department. The examination room terminal 5 is used to input information about examination data of examination performed in the examination room based on an examination order that has been input at each clinical department terminal 2. Standard software, such as an operating system, has been installed in the examination room terminal 5. Further, software for retrieving an examination order and inputting examination data has been installed in the examination room terminal 5. Information about examination data of examination performed in each examination room is input at the examination room terminal 5 in such a manner to be related to an examination order or a patient ID. Further, the clinical information management server 3, which will be described later, functions also as a server for managing information about examination data that have been input at the examination room terminal 5. The information about the input examination data is also stored, as clinical information S, in the clinical information database 32.

In the embodiment of the present disclosure, the graph display apparatus 1 includes the clinical information management server 3 and the clinical department terminal 2. Each of computers of the clinical information management server 3 and the clinical department terminal 2 is controlled by a graph display program installed from a recording medium, such as a CD-ROM, and functions as the graph display apparatus 1 in the embodiment of the present disclosure. The graph display program may be installed after being downloaded from a storage unit of a server connected through a network, such as the Internet. In FIG. 1, the clinical information management server 3 and the clinical department terminal 2 are directly connected to each other. Alternatively, the clinical information management server 3 and the clinical department terminal 2 may be connected to each other through the network 6.

The clinical information management server 3 is a computer including a clinical information database 32. The clinical information management server 3 is connected to the electronic chart management server 4 and the examination room terminal 5 through the network 6. The clinical information management server 3 obtains clinical information S, such as an electronic chart of a patient and various kinds of examination data, by retrieving it, based on the patient ID of the patient, from each connected server or the like. Further, the clinical information management server 3 stores clinical information S in such a manner to be related to each patient ID. When a patient has plural diseases, the clinical information management server 3 stores clinical information S related to the patient ID by classifying clinical information S for the plural diseases. The clinical information management server 3 updates clinical information S to be managed at fixed time every day.

An operating system and software for managing a database have been installed in the clinical information management server 3. Further, a program related to processing for determining a maximum line-connection interval in the graph display program according the embodiment of the present disclosure has been installed in the clinical information management server 3. When this program is executed, the clinical information management server 3 functions as a maximum line-connection interval determination means 31 that determines a maximum line-connection interval corresponding each examination with respect to plural examinations for diagnosis or diagnosis and treatment.

The clinical department terminal 2 is a computer used by a doctor of a clinical department or the like to retrieve clinical information S about a patient, to input an examination order or the like. The clinical department terminal 2 includes a display device, which is a general display, and an input device including a keyboard, a mouse and the like. Further, the clinical department terminal 2 is used also to display and refer to a graph representing a change in examination data of performed examination, and clinical information S, such as a generated electronic chart. Standard software, such as an operating system, and application software, such as a clinical information integrated display viewer for displaying clinical information S, such as a generated electronic chart, have been installed in the clinical department terminal 2.

Parts defining patient specification receipt processing, clinical information obtainment processing, line graph generation processing and graph display processing in the graph display program according to the embodiment of the present disclosure have been incorporated in the clinical information integrated viewer. When this graph display program is executed, the clinical department terminal 2 functions as the patient specification receipt means 21, the clinical information obtainment means 22, the line graph generation means 23 and the graph display means 24.

Further, graph generation information necessary to generate a time series graph for each disease has been set, in advance, in the clinical information integrated display viewer. The graph generation information includes a disease name, examination items of examination to be represented by graphs, a display range of a vertical axis of graphs, a display range of a horizontal axis of the graphs, colors, line types, marks, fonts and font sizes, which are necessary to generate graphs. The examination items represented by the graphs are plural examination items set in advance according to a disease, and which are considered to be important to diagnose the disease. Further, the display range of the vertical axis of the graph has been set based on possible values of examination data for each examination corresponding to an examination item. The display range of the horizontal axis of the graph in the graph generation information is determined after obtainment of clinical information S about each patient in such a manner that the display range coincides with a time period in which examination data about each patient are present. However, values other than the display range of the horizontal axis in the graph generation information have been set in advance.

Figure 2A:
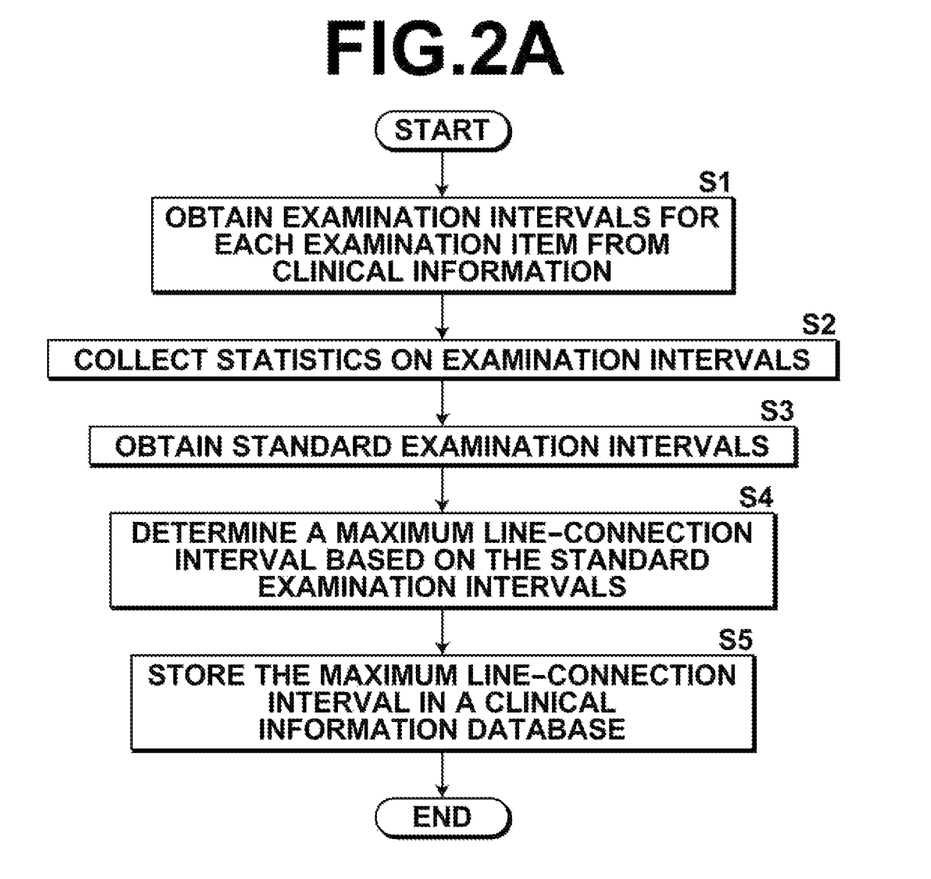
FIG. 2A is a flow chart showing a flow of processing for determining a maximum line-connection interval.
Figure 2B:
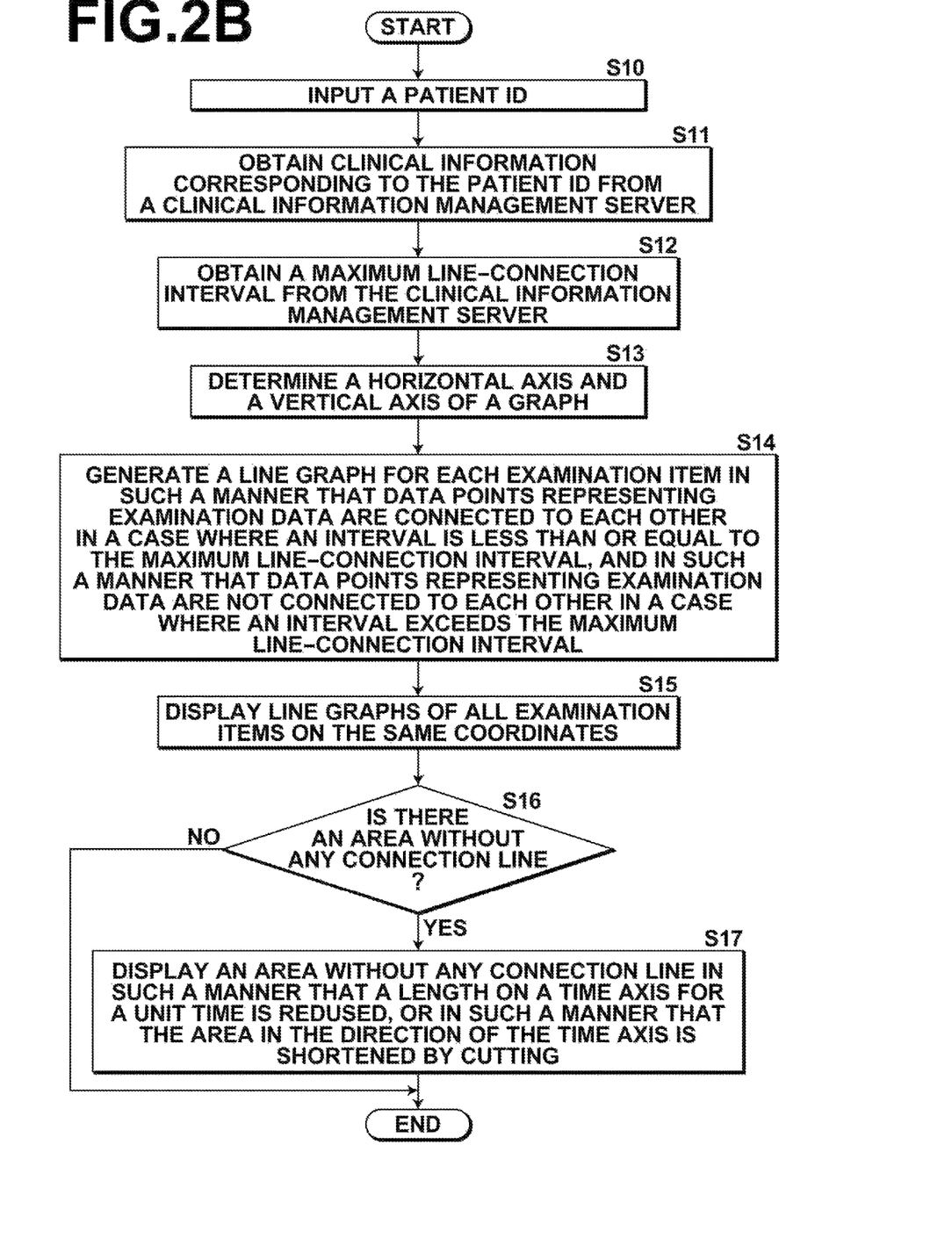
FIG. 2B is a flow chart showing a flow of processing for displaying graphs at a clinical department terminal.

FIG. 2A, FIG. 2B are flow charts showing flows of processing by the graph generation apparatus.

First, a flow of processing for determining a maximum line-connection interval in the clinical information management server 3 will be described with reference to FIG. 1 and FIG. 2A.

The maximum line-connection interval determination means 31 obtains cumulative frequencies of time intervals for each examination item i, and determines, as standard examination intervals, time intervals having ratios of cumulative frequencies to the total number of times of the examination (cumulative relative frequency) that are less than or equal to a predetermined threshold. Specifically, an examination interval at which examination Ti ($1 \leq i \leq n$: n is the number of kinds of examination) for examination item i was performed is obtained from each of plural pieces of clinical information S stored in the clinical information database 32 (S1). A frequency distribution of examination intervals of examination Ti is generated based on obtained plural examination intervals of examination Ti (S2). Here, when an examination interval is long, such as one year or longer, a probability that a patient was not regularly seeing a doctor in the time period is high. Therefore, the time period is excluded from statistics. A range of 98% of examination intervals at which examination Ti was performed may be considered, as standard examination intervals, while an average or a median of the examination intervals is considered as a center. Therefore, examination intervals to which 98% of the examination intervals belong are obtained, and set as standard examination intervals (S3). Further, a maximum value of the standard examination intervals is determined as maximum line-connection interval I (S4). Here, a range including 98% of examination intervals is regarded as the range of standard examination intervals. An appropriate threshold should be determined so that an interval that is not an ordinary interval of examination Ti is excluded from examination intervals of examination Ti. Maximum line-connection interval I for each examination item i is stored in the clinical information database 32 (S5).

Figure 3:
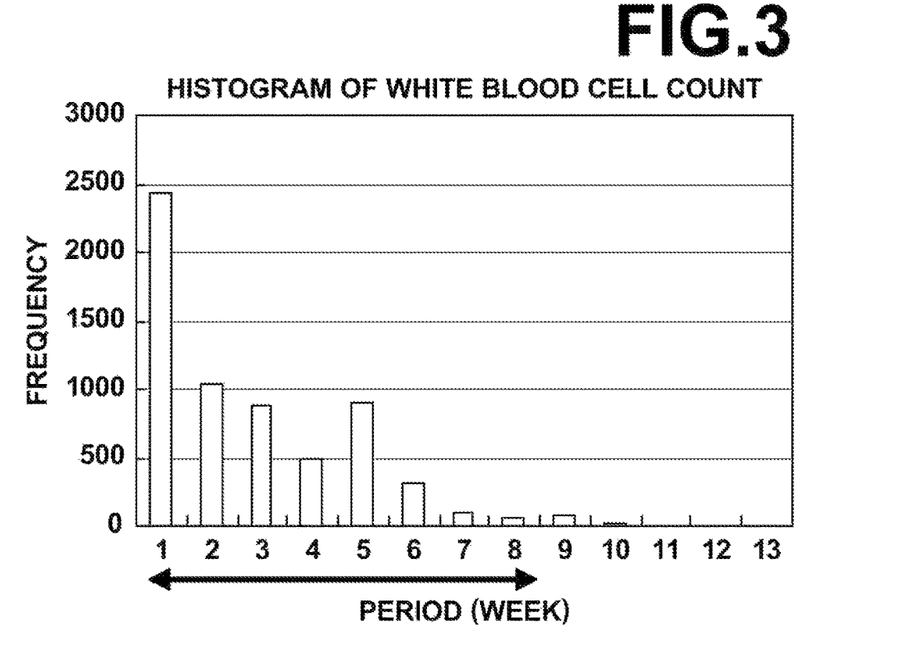
FIG. 3 is a frequency distribution histogram of white blood cell count.
Figure 4:
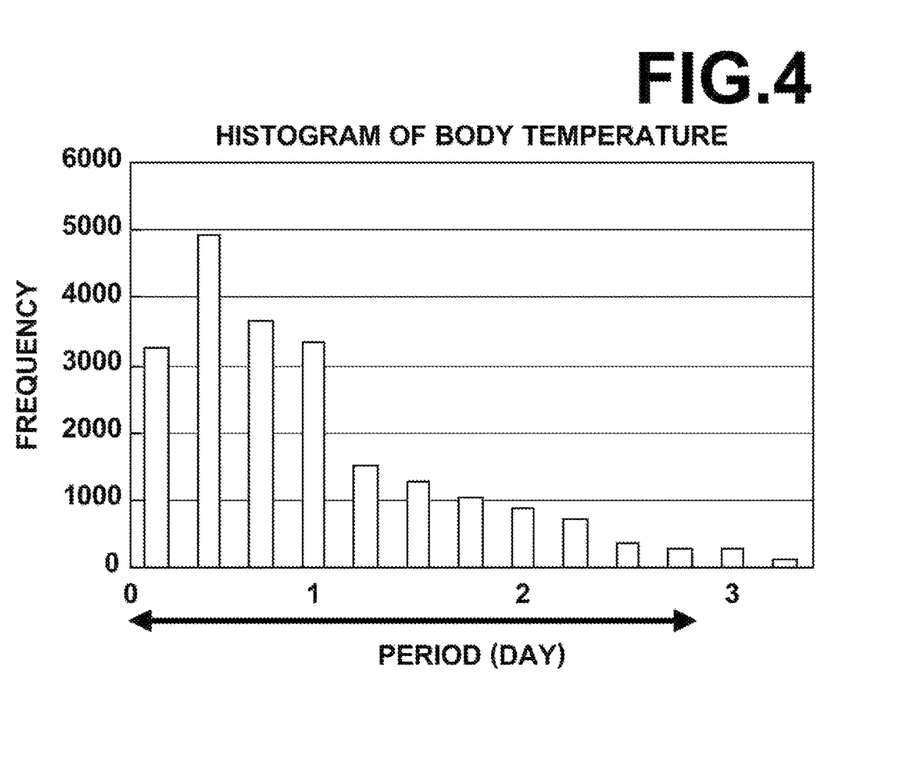
FIG. 4 is a frequency distribution histogram of body temperature.

Specific calculation methods for determining standard examination intervals and maximum line-connection intervals for body temperature and white blood cell count by using cumulative frequencies will be described by using the examples shown in Table 1 and Table 2. Table 1 shows frequencies (the numbers of times) of extraction of examination intervals for white blood cell count and cumulative relative frequencies. FIG. 3 is a frequency distribution histogram corresponding to Table 1. Table 2 shows frequencies (the numbers of times) of extraction of examination intervals for body temperature and cumulative relative frequencies. FIG. 4 is a frequency distribution histogram corresponding to Table 2. In FIGS. 3 and 4, a range indicated by an arrow at the bottom is a 98% interval.

TABLE 1

WHITE BLOOD CELL COUNT

| EXAMINATION INTERVAL (WEEK) | FREQUENCY | CUMULATIVE RELATIVE FREQUENCY |
|---|---|---|
| 1 | 2430 | 0.385 |
| 2 | 1045 | 0.55 |
| 3 | 881 | 0.69 |

TABLE 1-continued

WHITE BLOOD CELL COUNT

| EXAMINATION INTERVAL (WEEK) | FREQUENCY | CUMULATIVE RELATIVE FREQUENCY |
|---|---|---|
| 4 | 485 | 0.767 |
| 5 | 894 | 0.908 |
| 6 | 320 | 0.959 |
| 7 | 97 | 0.974 |
| 8 | 56 | 0.983 |
| 9 | 69 | 0.994 |
| 10 | 23 | 0.998 |
| 11 | 4 | 0.998 |
| 12 | 8 | 1 |
| 13 | 2 | 1 |
| TOTAL | 6314 | |

STATISTICAL TIME PERIOD 8 WEEKS

TABLE 2

BODY TEMPERATURE

| EXAMINATION INTERVAL (DAY) | FREQUENCY | CUMULATIVE RELATIVE FREQUENCY |
|---|---|---|
| 0.25 | 3243 | 0.15 |
| 0.5 | 4925 | 0.378 |
| 0.75 | 3640 | 0.546 |
| 1 | 3357 | 0.702 |
| 1.25 | 1509 | 0.771 |
| 1.5 | 1286 | 0.831 |
| 1.75 | 1032 | 0.879 |
| 2 | 875 | 0.919 |
| 2.25 | 732 | 0.953 |
| 2.5 | 340 | 0.969 |
| 2.75 | 293 | 0.982 |
| 3 | 263 | 0.994 |
| 3.25 | 121 | 1 |
| TOTAL | 21616 | |

STATISTICAL TIME PERIOD 3 DAYS

In the example of white blood cell count, shown in Table 1, the cumulative relative frequency exceeds 0.98 at the examination interval of about 8 weeks. Therefore, the standard examination intervals for white blood cell count are 8 weeks or less. Hence, maximum line-connection interval I is determined as 8 weeks. In the example of body temperature, shown in Table 2, the cumulative relative frequency exceeds 0.98 at the examination interval of 2.75 days. Further, maximum line-connection interval I is determined as 3 days to set a round number for convenience of displaying graphs. In the examples shown in Table 1 and Table 2, determined maximum line-connection intervals I are indicated by italic letters.

In the above descriptions, the method for determining a maximum line-connection interval based on a frequency distribution was explained. Next, a case of obtaining standard examination intervals by using standard deviation will be described, assuming that the distribution of examination intervals of examination data in the past is similar to a normal distribution. The maximum line-connection interval determination means 31 obtains plural examination intervals of examination Ti for each examination item i (S1). The maximum line-connection interval determination means 31 obtains, based on the obtained examination intervals of examination Ti, average $\mu$ and variance $\sigma^2$ of examination intervals of examination Ti (S2). Examination intervals belonging to an interval of 98% of the normal distribution are standard examination intervals, and the interval of 98% is in the range of about 2.05*σ (standard deviation). In other words, $$\text{Standard Examination Intervals} \le \mu + 2.05 \times \sigma \qquad (1)$$

(S3).

The longest examination interval of the standard examination intervals is determined as maximum line-connection interval I (S4). Maximum line-connection interval I for each examination item i is stored in the clinical information database 32 (S5).

Table 3 shows average μ, standard deviation σ and an interval including 98% of examination data for body temperature and white blood cell count. When the average examination interval for white blood cell count is 2.8 weeks, and standard deviation is 2.0 weeks, a 98% interval, which corresponds to standard examination intervals, is 6.9 weeks by using expression (1). Therefore, maximum line-connection interval I is determined as 6.9 weeks. Meanwhile, an average of examination intervals for body temperature is 1.0 day, and standard deviation is 0.7 day. Therefore, a 98% interval, which corresponds to standard examination intervals, is 2.4 days by using expression (1), and a maximum line-connection interval is determined as 2.4 days. A time interval within a predetermined range from the maximum value of standard examination intervals should be determined as the maximum line-connection interval. For example, maximum line-connection interval I for white blood cell count may be determined as 7 weeks, and maximum line-connection interval I for body temperature may be determined as 3 days to set round numbers.

TABLE 3

|  | WHITE BLOOD CELL | BODY TEMPERATURE |
|---|---|---|
| AVERAGE | 2.8 WEEKS | 1.0 DAY |
| STANDARD DEVIATION | 2.0 WEEKS | 0.7 DAY |
| STANDARD EXAMINATION INTERVAL (98% INTERVAL) | 6.9 WEEKS | 2.4 DAY |

In the above descriptions, calculation was performed by assuming that examination intervals follow a normal distribution, However, the examination intervals do not always follow a normal distribution. In some actual cases, a 98% interval obtained by using a normal distribution and a 98% interval obtained by using cumulative frequency differ from each other. Therefore, an examination interval appropriately adjusted, based on experiences, within a predetermined range from the maximum value in the 98% interval obtained in a normal distribution may be determined, as the maximum line-connection interval.

In the above descriptions, the distribution of examination intervals was assumed to follow a normal distribution. More accurately, it is desirable to use a gamma distribution or the like.

In the above descriptions, a case in which the maximum line-connection interval is determined not according to a disease, but based on examination intervals for an examination item was described. However, examination intervals for the same examination item are different depending on a disease in some cases. Therefore, a maximum line-connection interval may be determined by collecting statistics of each examination item for each disease.

Further, in the above descriptions, a case in which the maximum line-connection is determined based on examination intervals of examination for an examination item performed on many patients was described. However, an examination interval for each examination item should be determined for each patient in some cases. Therefore, the maximum line-connection interval may be determined for an examination item of each patient.

Alternatively, the maximum line-connection interval for each examination item may be input in advance at an input device, and stored in the clinical information database 32 or the clinical information integrated display viewer. The maximum line-connection interval determination means determines the maximum line-connection interval by obtaining the stored maximum line-connection interval.

Next, a flow of processing for displaying graphs at the clinical department terminal 2 will be described with reference to FIG. 1 and FIG. 2B.

A doctor in a clinical department inputs a patient ID into an input box displayed on a display screen of a display device at the clinical department terminal 2 to check clinical information S about a patient to be diagnosed (S10). The input patient ID is received by the patient specification receipt means 21, and a clinical information integrated viewer of the patient is displayed on the display screen. The clinical information obtainment means 22 obtains, based on the received patient ID, clinical information S corresponding to the patient ID from the clinical information database 32 in the clinical information management server 3, and stores clinical information S in a memory of the clinical department terminal 2 (S11). Further, the clinical information obtainment means 22 obtains a disease name of the patient from an electronic chart included in obtained clinical information S.

The line graph generation means 23 extracts, based on graph generation information corresponding to the disease of the patient, examination data for plural examination items i corresponding to the disease, which are set in the graph generation information, from obtained clinical information S about the patient to be diagnosed. Further, the line graph generation means 23 obtains maximum line-connection interval I corresponding to each of plural examination items i from the clinical information database 32 in the clinical information management server 3 (S12).

The graph display means 24 determines a display range of the horizontal axis and the vertical axis of the graph and scales on each of the axes (S13). Scales on the vertical axis of the graph are assigned based on the range of possible examination values of examination data for each examination item i displayed by the graph. Since the range of possible examination values differs in each examination item i, scales on the vertical axis are different in each examination item i. Further, the scales of the vertical axis are assigned in such a manner that line graphs of examination items i do not overlap with each other. The horizontal axis is used as a time axis, and the display range of the horizontal axis is a whole time period in which examination data for any one of the examination items about the patient are present. Alternatively, a doctor may input a display period of graphs at the input device, and the display range of the horizontal axis of graphs may be determined based on the input display period.

Next, the line graph generation means 23 generates, on coordinates defined by a vertical axis representing examination values and a horizontal axis as a time axis, a line graph in such a manner that data points representing examination data are connected to each other by using a color, a line type and marks (marks indicating positions of data points representing examination data, such as ○ and ■), which have been determined for each examination item i. The line graph is generated based on maximum line-connection interval I corresponding to each examination item i. Data points representing examination data are connected to each other in a case where a time interval between examinations temporally next to each other is less than or equal to maximum line-connection interval I, but data points representing examination data are not connected to each other in a case where the time interval between examinations temporally next to each other exceeds maximum line-connection interval I (S14).

Finally, the graph display means 24 displays generated line graphs for all of examination items i on the same coordinates (S15). Meanwhile, a time period without any connection line in a graph is a time period without any meaningful data. Therefore, when an area without any connection line in all of the line graphs for examination items i is present (S16), the area is displayed in such a manner that a length on the time axis for a unit time is reduced. Alternatively, the area is displayed in such a manner that the area in the direction of the time axis is shortened by cutting (S17). Accordingly, it is possible to display a change in data for a longer period of time on a display screen. Therefore, observation of line graphs in a time period in which examination data are present becomes easy. Further, it is possible to easily check a clinical history.

Figure 5:
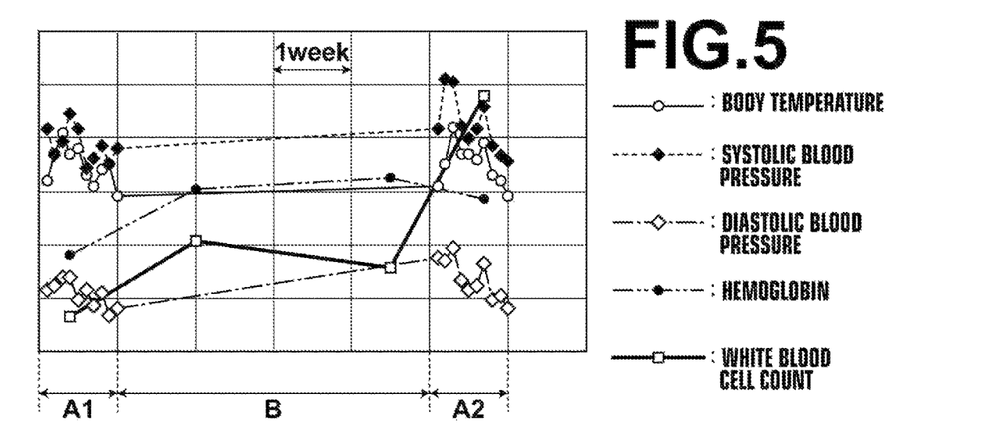
FIG. 5 is an example of line graphs in which all data points representing examination data are connected by lines.

Here, specific examples of line graphs will be described with reference to FIG. 5 through FIG. 8. FIG. 5 illustrates an example in which all data points representing examination data for examination items are connected by lines. In the line graphs, a solid line represents body temperature, a broken line represents systolic blood pressure, a dot dashed line represents diastolic blood pressure, two-dot dashed line represents hemoglobin, and a bold line represents white blood cell count. In FIG. 5 through FIG. 8, a square box on the horizontal axis represents one week. In FIG. 5, a patient is hospitalized in time period A1 and time period A2. Therefore, vital (body temperature and blood pressure) data are present in the time periods. Examinations for hemoglobin and white blood cell count are regularly performed in the whole time period of A1, B and A2, regardless of whether the patient is hospitalized.

Figure 6:
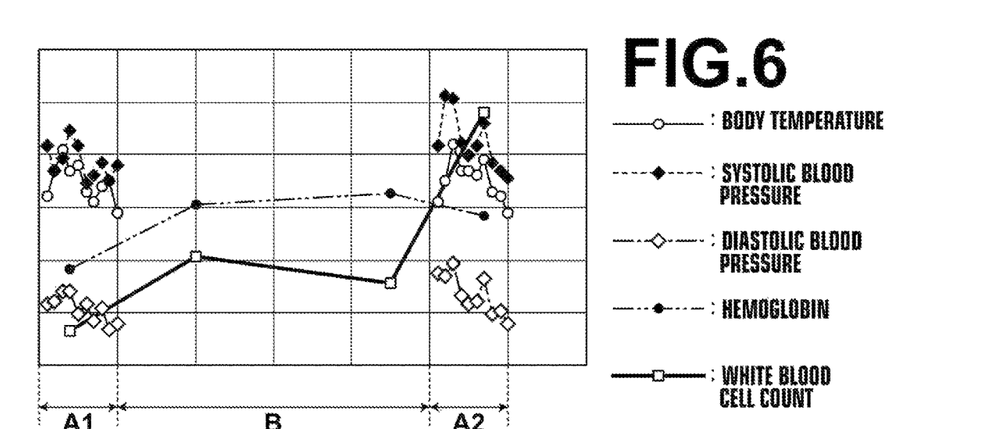
FIG. 6 is an example of line graphs in which data points representing examination data exceeding a maximum line-connection interval are not connected by lines.

FIG. 6 illustrates an example in which line connection of graphs illustrated in FIG. 5 has been controlled by using the graph generation apparatus 1 of the present disclosure. When maximum line-connection interval I of body temperature is 3 days, data points representing examination data for body temperature are not connected to each other by lines in time period B in which a time interval of examinations temporally next to each other exceeds maximum line-connection interval I. When maximum line-connection interval I of blood pressure is 4 days, data points representing examination data for blood pressure are not connected to each other by lines in time period B in the same manner to body temperature. Maximum line-connection intervals I of white blood cell count and hemoglobin are 8 weeks. Therefore, data points are connected to each other in time period B.

Figure 7:
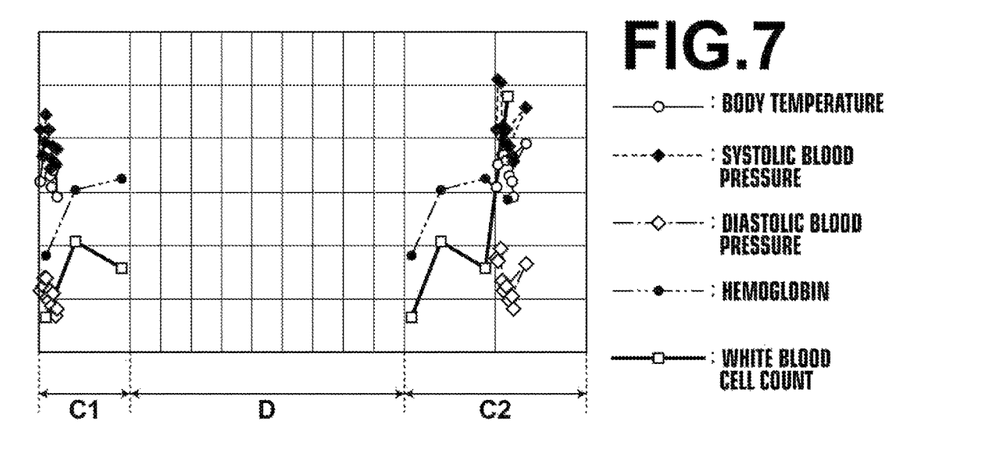
FIG. 7 is an example of line graphs in which a length on a time axis is reduced in a time period without any connection line.
Figure 8:
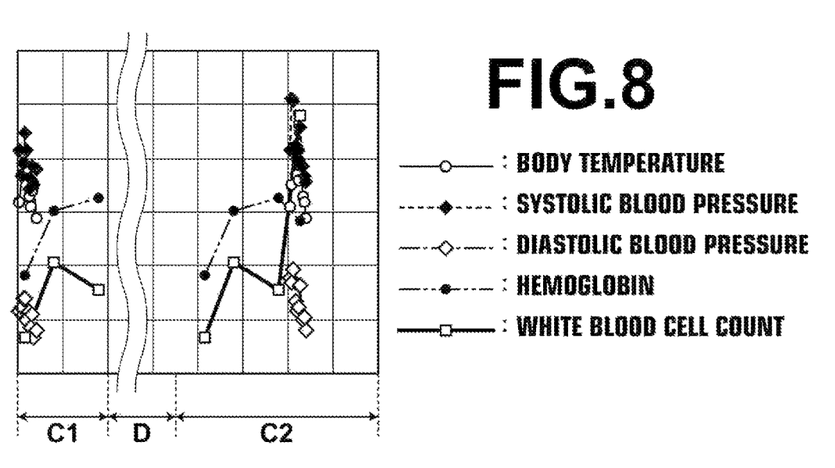
FIG. 8 is an example of line graphs in which a time period without any connection line is shortened in the direction of the time axis by cutting.

FIG. 7 illustrates an example of display in which a length on a time axis in an area without any connection line is reduced by using the graph generation apparatus 1 of the present disclosure. The maximum line-connection interval of white blood vessel count is 8 weeks. Therefore, in a case where there is no examination data in time period D (9 weeks), data points are not connected to each other also for white blood cell count. Similarly, data points are not connected to each other also for hemoglobin. Since there are no examination data in this time period, no observation is needed in this time period. Therefore, in the coordinates, a length on the time axis for a unit time is reduced in an area in time period D, in which no connection line is present in all the line graphs for the examination items, compared with time periods C1, C2, in which connection lines are present. Alternatively, as illustrated in FIG. 8, the area of time period D, in which no connection line is present in all the line graphs for the examination items, may be displayed in such a manner that area is shortened in the direction of the time axis by cutting.

The present disclosure is not limited to embodiments of the present disclosure. A part or all of composition elements of the graph generation apparatus may be configured by a workstation, or by at least one workstation, a server and a storage unit connected to each other through a network. Here, each equipment is controlled by a program for generating a graph as described in the specification of the present application, and which is installed from a recording medium, such as a CD-ROM. The program may be installed after being downloaded from a storage unit of a server connected through a network, such as the Internet.

What is claimed is:

1. A graph display apparatus that displays, on a same coordinate having a horizontal axis and a vertical axis, one of which is a time axis and the other one is an axis of examination values, line graphs connecting data points representing examination data about a patient by lines in order of time of examination for a plurality of examination items, the apparatus comprising:
 a processor configured to
  determine, for each of the plurality of examination items, a maximum line-connection interval that is a longest time interval between examinations temporally next to each other to connect data points representing examination data for the each of the plurality of examination items to each other, and
 generate a line graph for each of the plurality of examination items in such a manner that data points representing examination data are connected to each other in a case where a time interval between examinations temporally next to each other is less than or equal to the maximum line-connection interval for the each of the plurality of examination items, and in such a manner that data points representing examination data are not connected to each other in a case where the time interval between examinations temporally next to each other exceeds the maximum line-connection interval for the each of the plurality of examination items, wherein the processor is further configured to obtain, for each of the plurality of examination items, examination intervals between examinations performed on a plurality of patients, and sets, for each of the plurality of examination items, examination intervals within a predetermined range from an average or a median of the obtained examination intervals, as standard examination intervals, and determines a time interval within a predetermined range from a maximum value of the standard examination intervals, as the maximum line-connection interval; and
 a graph display unit that displays the line graphs on the same coordinate.

2. The graph display apparatus, as defined in claim 1, wherein the graph display unit displays an area in a time period without any connection line in all the line graphs for the plurality of examination items in such a manner that a length on a time axis for a unit time is reduced, or in such a manner that the area in the direction of the time axis is shortened by cutting.

3. The graph display apparatus, as defined in claim 1, wherein the maximum line-connection interval is determined according to a disease.

4. The graph display apparatus, as defined in claim 1, wherein the processor is capable of generating the line graph comprising data points representing examination data of a part of the plurality of examination items connected to each other in the case where the time interval between examinations temporally next to each other is less than or equal to the maximum line-connection interval and data points representing examination data of the other part of the plurality of examination items without being connected to each other in the case where the time interval between examinations temporally next to each other exceeds the maximum line-connection interval.

5. An operation method of a graph display apparatus that displays, on a same coordinate having a horizontal axis and a vertical axis, one of which is a time axis and the other one is an axis of examination values, line graphs connecting data points representing examination data about a patient by lines in order of time of examination for a plurality of examination items, the method comprising:
   a maximum line-connection interval determination step in which by using a processor determines, for each of the plurality of examination items, a maximum line-connection interval that is a longest time interval between examinations temporally next to each other to connect data points representing examination data for the each of the plurality of examination items to each other;
   a line graph generation step in which by using the processor generates a line graph for each of the plurality of examination items in such a manner that data points representing examination data are connected to each other in a case where a time interval between examinations temporally next to each other is less than or equal to the maximum line-connection interval for the each of the plurality of examination items, and in such a manner that data points representing examination data are not connected to each other in a case where the time interval between examinations temporally next to each other exceeds the maximum line-connection interval for the each of the plurality of examination items, wherein the processor is further configured to obtain, for each of the plurality of examination items, examination intervals between examinations performed on a plurality of patients, and sets, for each of the plurality of examination items, examination intervals within a predetermined range from an average or a median of the obtained examination intervals, as standard examination intervals, and determines a time interval within a predetermined range from a maximum value of the standard examination intervals, as the maximum line-connection interval; and
   a graph display step in which a graph display unit displays the line graphs on the same coordinate.

6. The operation method, as defined in claim 5, wherein the processor is capable of generating the line graph comprising data points representing examination data of a part of the plurality of examination items connected to each other in the case where the time interval between examinations temporally next to each other is less than or equal to the maximum line-connection interval and data points representing examination data of the other part of the plurality of examination items without being connected to each other in the case where the time interval between examinations temporally next to each other exceeds the maximum line-connection interval.

7. A non-transitory recording medium having stored therein a graph display program that causes a computer of a graph display apparatus that displays, on a same coordinate having a horizontal axis and a vertical axis, one of which is a time axis and the other one is an axis of examination values, line graphs connecting data points representing examination data about a patient by lines in order of time of examination for a plurality of examination items to:
   determine, for each of the plurality of examination items, a maximum line-connection interval that is a longest time interval between examinations temporally next to each other to connect data points representing examination data for the each of the plurality of examination items to each other;
   generate a line graph for each of the plurality of examination items in such a manner that data points representing examination data are connected to each other in a case where a time interval between examinations temporally next to each other is less than or equal to the maximum line-connection interval for the each of the plurality of examination items, and in such a manner that data points representing examination data are not connected to each other in a case where the time interval between examinations temporally next to each other exceeds the maximum line-connection interval for the each of the plurality of examination items, wherein the processor is further configured to obtain, for each of the plurality of examination items, examination intervals between examinations performed on a plurality of patients, and sets, for each of the plurality of examination items, examination intervals within a predetermined range from an average or a median of the obtained examination intervals, as standard examination intervals, and determines a time interval within a predetermined range from a maximum value of the standard examination intervals, as the maximum line-connection interval; and
   a graph display unit that displays the line graphs on the same coordinate.

8. The non-transitory recording medium, as defined in claim 7, wherein the computer is capable of generating the line graph comprising data points representing examination data of a part of the plurality of examination items connected to each other in the case where the time interval between examinations temporally next to each other is less than or equal to the maximum line-connection interval and data points representing examination data of the other part of the plurality of examination items without being connected to each other in the case where the time interval between examinations temporally next to each other exceeds the maximum line-connection interval.

* * * * *